United States Patent [19]

Holmwood et al.

[11] Patent Number: 4,738,962
[45] Date of Patent: Apr. 19, 1988

[54] PIPERAZINYLMETHYL-1,2,4-TRIAZOLYL-METHYL-CARBINOL FUNGICIDES

[75] Inventors: Graham Holmwood, Wuppertal; Karl H. Büchel, Burscheid; Wilhelm Brandes, Leichlingen; Paul Reinecke, Leverkusen, all of Fed. Rep. of Germany

[73] Assignee: Bayer Aktiengesellschaft, Leverkusen, Fed. Rep. of Germany

[21] Appl. No.: 832,502

[22] Filed: Feb. 21, 1986

[30] Foreign Application Priority Data

Mar. 13, 1985 [DE] Fed. Rep. of Germany ....... 3508909

[51] Int. Cl.$^4$ ................ A61K 31/495; C07D 401/14; C07D 403/14
[52] U.S. Cl. .................................... 514/252; 514/253; 544/295; 544/333; 544/360; 544/362; 544/364; 544/366; 544/225
[58] Field of Search ............... 544/362, 363, 366, 295, 544/333, 360, 364, 225; 514/252, 253

[56] References Cited

U.S. PATENT DOCUMENTS 4,331,674  5/1982  Krämer et al. .................... 544/366

FOREIGN PATENT DOCUMENTS 0068144  1/1983  European Pat. Off. .
0110048  6/1984  European Pat. Off. .
0114487  8/1984  European Pat. Off. .

*Primary Examiner*—Donald G. Daus
*Assistant Examiner*—Cecilia Shen
*Attorney, Agent, or Firm*—Sprung Horn Kramer & Woods

[57] ABSTRACT

Fungicidally active novel piperazinylmethyl-1,2,4-triazolylmethyl-carbinols of the formula

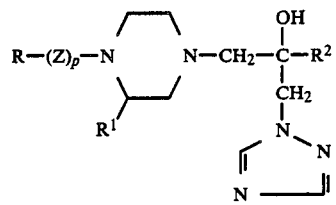

in which
R represents optionally substituted alkyl, optionally substituted alkenyl, optionally substituted alkinyl, optionally substituted cycloalkyl, optionally substituted aryl, optionally substituted aralkyl, optionally substituted aryloxyalkyl or optionally substituted arylthioalkyl,
$R^1$ represents hydrogen or alkyl,
$R^2$ represents optionally substituted alkyl, optionally substituted alkenyl, optionally substituted cycloalkyl, optionally substituted aryl or optionally substituted heterocyclyl,
Z represents the

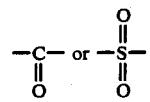

group and
p represents the number 0 or 1,
or addition products thereof with acids and metal salts.

10 Claims, No Drawings

PIPERAZINYLMETHYL-1,2,4-TRIAZOLYLMETHYL-CARBINOL FUNGICIDES

The invention relates to new piperazinylmethyl-1,2,4-triazolylmethyl-carbinols, a process for their preparation, and their use as plant protection agents.

It is already known that certain triazolylmethyl-carbinols possess fungicidal properties (see U.S. Ser. No. 549,867, filed Nov. 8, 1983). Thus, for example, 3,3-dimethyl-2-phenoxymethyl-1-(1,2,4-triazol-1 -yl)-butan-2-ol and 2-[(3,4-dichlorophenoxy)-methyl]-3,3-dimethyl-1-(1,2,4-triazol-1-yl)-butan-2-ol can be used for combating fungi and other undesired microorganisms. However, the action of these previously known compounds is not always completely satisfactory in all fields of use, particularly where small amounts and low concentrations are employed.

New piperazinylmethyl-1,2,4-triazolylmethyl-carbinols of the formula

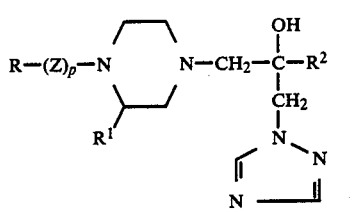

in which

R represents optionally substituted alkyl, optionally substituted alkenyl, optionally substituted alkinyl, optionally substituted cycloalkyl, optionally substituted aryl, optionally substituted aralkyl, optionally substituted aryloxyalkyl or optionally substituted arylthioalkyl, $R^1$ represents hydrogen or alkyl, $R^2$ represents optionally substituted alkyl, optionally substituted alkenyl, optionally subtituted cycloalkyl optionally substituted aryl or optionally substituted heterocyclyl, Z represents the

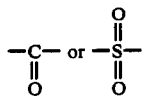

group and p represents the number 0 or 1, and their acid addition salts and metal salt complexes have now been found.

It has also been found that the new piperazinylmethyl-1,2,4-triazolylmethyl-carbinols of the formula (I) and their acid addition salts and metal salt complexes are obtained if triazolylmethyloxiranes of the formula

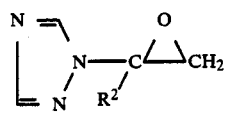

in which $R^2$ has the meaning given above, are reacted with substituted piperazines of the formula

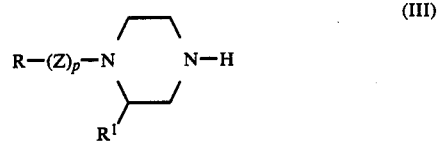

in which R, $R^1$, Z and p have the meaning given above, if appropriate in the presence of a diluent and, if appropriate, in the presence of a catalyst, and, if required, the product is then subjected to an addition reaction with an acid or a metal salt.

Finally, it has been found that the new piperazinylmethyl-1,2,4-triazolylmethyl-carbinols of the formula (I) possess very good fungicidal properties.

Surprisingly, the piperazinylmethyl-1,2,4-triazolylmethyl-carbinols according to the invention, of the formula (I), exhibit a substantially better fungicidal activity than 3,3-dimethyl-2-phenoxymethyl-1-(1,2,4-triazol-1-yl)-butan-2-ol and 2-[(3,4-dichlorophenoxy)-methyl]-3,3-dimethyl-1-(1,2,4-triazol-1-yl)-butan-2-ol, which are chemically similar substances known from the prior art and having a similar action.

Formula (I) gives a general definition of the piperazinylmethyl-1,2,4-triazolylmethyl-carbinols according to the invention. Preferred compounds of the formula (I) are those in which R represents straight-chain or branched alkyl having 1 to 12 carbon atoms, straight-chain or branched alkenyl having 2 to 12 carbon atoms, straight-chain or branched alkinyl having 2 to 12 carbon atoms, alkoxyalkyl having 1 to 8 carbon atoms in the alkyl part and 1 to 8 carbon atoms in the alkoxy part, alkylthioalkyl having 1 to 8 carbon atoms in the alkyl part and 1 to 8 carbon atoms in the alkylthio part, halogenoalkyl having 1 to 8 carbon atoms and 1 to 17 identical or different halogen atoms, halogenoalkoxyalkyl having 1 to 8 carbon atoms in the alkyl part and 1 to 8 carbon atoms in the halogenoalkoxy part and 1 to 17 identical or different halogen atoms, halogenoalkylthioalkyl having 1 to 8 carbon atoms in the alkyl part and 1 to 8 carbon atoms in the halogenoalkylthio part and 1 to 17 identical or different halogen atoms, cycloalkyl which has 3 to 7 ring carbon atoms and is optionally monosubstituted or polysubstituted by identical or different alkyl radicals of 1 to 4 carbon atoms, or represents aryl having 6 to 10 carbon atoms, aralkyl having 6 to 10 carbon atoms in the aryl part and 1 to 4 carbon atoms in the alkyl part, aryloxyalkyl having 6 to 10 carbon atoms in the aryloxy part and 1 to 4 carbon atoms in the alkyl part, or arylthioalkyl having 6 to 10 carbon atoms in the arylthio part and 1 to 4 carbon atoms in the alkyl part, it being possible for each of the abovementioned aryl radicals to be monosubstituted or polysubstituted by identical or different substituents from amongst halogen, straight-chain or branched alkyl having 1 to 4 carbon atoms, alkoxy having 1 to 4 carbon atoms, alkylthio having 1 to 4 carbon atoms, halogenoalkyl having 1 to 4 carbon atoms and 1 to 9 identical or different halogen atoms, halogenoalkoxy having 1 to 4 carbon atoms and 1 to 9 identical or different halogen atoms, halogenoalkylthio havi 1 to 4 carbon atoms and 1 to 9 identical or different halogen atoms, cycloalkyl having 3 to 7 ring carbon atoms, phenyl which is optionally substituted by halogen and/or alkyl having 1 to 4 carbon atoms, phenylalkyl which has 1 to 4 carbon atoms in the alkyl part and is optionally substituted by halogen and/or alkyl having 1 to 4 carbon atoms, phenylalkoxy which has 1 to 4 carbon atoms in the alkoxy part and is optionally substituted by halogen and/or alkyl having 1 to 4 carbon atoms, and phenoxyalkyl which has 1 to 4 carbon atoms in the alkyl part and is optionally substituted by halogen and/or alkyl having 1 to 4 carbon atoms, $R^1$ represents hydrogen or straight-chain or branched alkyl having 1 to 4 carbon atoms, $R^2$ represents a straight-chain or branched alkyl having 1 to 8 carbon atoms, straight-chain or branched alkenyl having 2 to 8 carbon atoms, or represents cycloalkyl which has 3 to 7 ring carbon atoms and is optionally monosubstituted or polysubstituted by alkyl having 1 or 2 carbon atoms, or represents phenyl or naphthyl, it being possible for each of the two radicals mentioned above to be monosubstituted or polysubsituted by identical or different substituents from amongst halogen, straight-chain or branched alkyl having 1 to 4 carbon atoms and halogenoalkyl having 1 or 2 carbon atoms and 1 to 5 identical or different halogen atoms, such as fluorine atoms and chlorine atoms, and $R^2$ furthermore represents a 5-membered or 6-membered, optionally benzofused heterocyclic structure having 1 to 3 identical or different hetero atoms, such as oxygen, nitrogen and sulphur, it being possible for the heterocyclic structure to be monosubstituted or polysubstited by identical or different substituents from amongst halogen, alkyl having 1 to 4 carbon atoms and halogenoalkyl having 1 or 2 carbon atoms and 1 to 5 identical or different halogen atoms, such as fluorine atoms or chlorine atoms, and $R^2$ furthermore represents the radicals of the formulae

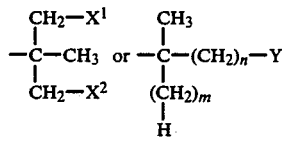

wherein $X^1$ represents hydrogen or halogen, $X^2$ represents halogen,

Y represents straight-chain or branched alkyl having 1 to 6 carbon atoms, alkoxy having 1 to 6 carbon atoms, alkylthio having 1 to 6 carbon atoms, halogenoalkoxy having 1 to 6 carbon atoms and 1 to 9 identical or different halogen atoms, halogenoalkylthio having 1 to 6 carbon atoms and 1 to 9 identical or different halogen atoms, alkenyl having 2 to 6 carbon atoms, straight-chain or branched alkoxycarbonyl having 1 to 4 carbon atoms in the alkoxy part, or cyano, or represents phenyl, phenoxy, pyridyloxy, phenylthio, phenylalkoxy having 1 to 4 carbon atoms in the alkoxy group and phenylalkylthio having 1 to 4 carbon atoms in the alkylthio group, it being possible for each of the abovementioned phenyl or pyridyl radicals to be monosubstituted or polysubstituted by identical or different substituents from amongst halogen, alkyl having 1 or 2 carbon atoms, alkoxy having 1 or 2 carbon atoms, alkylthio having 1 or 2 carbon atoms, halogenoalkyl having 1 or 2 carbon atoms and 1 to 5 identical or different halogen atoms, such as fluorine atoms and chlorine atoms, halogenoalkoxy having 1 or 2 carbon atoms and 1 to 5 identical or different halogen atoms, such as fluorine atoms and chlorine atoms, halogenoalkylthio having 1 or 2 carbon atoms and 1 to 5 identical or different halogen atoms, such as fluorine atoms and chlorine atoms, cycloalkyl having 3 to 7 carbon atoms, dialkylamino having 1 to 4 carbon atoms in each alkyl part, cyano, nitro and straight-chain or branched alkoxycarbonyl having 1 to 4 carbon atoms in the alkoxy part, and m represents the number 0 or 1, n represents the number 0, 1 or 2, Z represents the

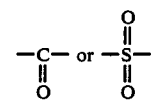

group, and p represents the number 0 or 1.

Particularly preferred compounds of the formula (I) are those in which

R represents straight-chain or branched alkyl having 1 to 8 carbon atoms, straight-chain or branched alkenyl having 2 to 8 carbon atoms, straight-chain or branched alkinyl having 2 to 8 carbon atoms, alkoxyalkyl having 1 to 4 carbon atoms in the alkyl part and 1 to 4 carbon atoms in the alkoxy part, alkylthioalkyl having 1 to 4 carbon atoms in the alkyl part and 1 to 4 carbon atoms in the alkylthio part, halogenoalkyl having 1 to 4 carbon atoms and 1 to 9 identical or different halogen atoms, halogenoalkoxyalkyl having 1 to 4 carbon atoms in the alkyl part and 1 to 4 carbon atoms in the halogenoalkoxy part and 1 to 9 identical or different halogen atoms, halogenoalkylthioalkyl having 1 to 4 carbon atoms in the alkyl part and 1 to 4 carbon atoms in the halogenoalkylthio part and 1 to 9 identical or different halogen atoms, or represents cyclopropyl, cyclopentyl or cyclohexyl, each of which is optionally monosubstituted to trisubstituted by identical or different substituents from amongst methyl, ethyl, n- and i-propyl and n-, i-, s- and t-butyl, or represents phenylethyl, benzyl, phenoxymethyl, phenoxyethyl, phenylthiomethyl, phenylthioethyl, phenyl or naphthyl, it being possible for each of the abovementioned aromatic radicals to be monosubstituted to trisubstituted by identical or different substituents from amongst fluorine, chlorine, bromine, iodine, methyl, ethyl, n- and i-propyl, n-, i-, s- and t-butyl, methoxy, ethoxy, n- and i-propoxy, methylthio, ethylthio, trifluoromethyl, trifluoromethoxy, trifluoromethylthio, cyclopropyl, cyclopentyl, cyclohexyl and phenyl, benzyl, benzyloxy and phenoxymethyl, it being possible for each of the 4 last-mentioned radicals to be monosubstituted to trisubstituted in the phenyl part by identical or different substituents from amongst fluorine, chlorine, bromine, methyl, ethyl and/or isopropyl, $R^1$ represents hydrogen, methyl, ethyl, n- or i-propyl, $R^2$ represents methyl, ethyl, n- or i-propyl, n-, i-, s- or t-butyl, or i-pentyl, or represents cyclopropyl, cyclopentyl or cyclohexyl, each of which is monosubstituted by methyl or ethyl or disubstituted or trisubstituted by identical or different substituents from amongst methyl and ethyl, or represents phenyl or naphthyl, it being possible for each of the two abovementioned radicals to be monosubstituted to trisubstituted by identical or different substituents from amongst fluorine, chlorine, bromine, iodine, methyl, ethyl, n-propyl, isopropyl, trifluoromethyl and trichloromethyl and trifluoromethoxy, and $R^2$ furthermore represents pyridyl, pyrimidyl or thienyl, each of which is optionally monosubstituted to trisubstituted by identical or different substituents, fluorine, chlorine, bromine, iodine, methyl, ethyl, n-propyl, iso-propyl, trifluoromethyl, trifluoromethoxy and trichloromethyl being mentioned as substituents, $R^2$ furthermore represents radicals of the formulae

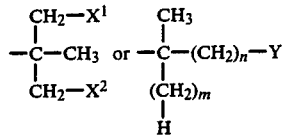

wherein $X^1$ represents hydrogen or halogen, $X^2$ represents halogen,

Y represents methyl, ethyl, n- or i-propyl, methoxy, ethoxy, methylthio, ethylthio, trifluoromethoxy, trifluoromethylthio, vinyl, allyl, methoxycarbonyl, ethoxycarbonyl or cyano, or represents phenyl, phenoxy, phenylthio, benzyloxy or benzylthio, it being possible for each of the five last-mentioned radicals to be monosubstituted to trisubstituted in the phenyl part by identical or different substituents from amongst fluorine, chlorine, bromine, methyl, ethyl, methoxy, methylthio, trifluoromethyl, trifluoromethoxy, trifluoromethylthio, dimethylamino, diethylamino, methoxycarbonyl, ethoxycarbonyl, cyano or nitro, and Y furthermore represents pyridyloxy which is optionally substituted by chlorine, m represents the number 0 or 1, n represents the number 0, 1 or 2, Z represents the

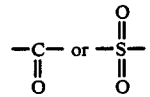

group, and p represents the number 0 or 1.

Other preferred compounds according to the invention are addition products of acids and those piperazinylmethyl-1,2,4-triazolylmethyl-carbinols of the formula (I) in which the substituents R, $R^1$, $R^2$, Z and p have the meanings which have already been mentioned as being preferred for these substituents.

The acids which can be used for the addition reactions preferably include hydrohalic acids, such as, for example, hydrochloric acid and hydrobromic acid, in particular hydrochloric acid, and phosphoric acid, nitric acid, monofunctional, bifunctional and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and naphthalene-1,5-disulphonic acid.

Other preferred compounds according to the invention are addition products of salts of metals of main groups II to IV and subgroups I and II and IV to VIII of the Periodic Table of Elements and those piperazinylmethyl-1,2,4-triazolylmethyl-carbinols of the formula (I) in which the substituents R, $R^1$, $R^2$, Z and p have the meanings which have already been mentioned as being preferred for these substituents.

Salts of copper, of zinc, of manganese, of magnesium, of tin, of iron and of nickel are particularly preferred in this respect. Suitable anions for these salts are those which are derived from acids which lead to physiologically acceptable addition products. In this connection, particularly preferred acids of this type are the hydrohalic acids, such as, for example, hydrochloric acid and hydrobromic acid, as well as phosphoric acid, nitric acid and sulphuric acid.

In addition to the compounds mentioned in the preparation examples, the following piperazinylmethyl-1,2,4-triazolylmethyl-carbinols of the formula (I) may be mentioned individually:

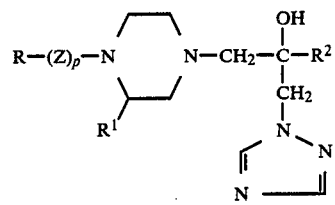

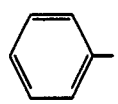

-continued $$\begin{array}{c} \text{R—(Z)}_p\text{—N} \underset{R^1}{\overset{}{\bigcirc}} \text{N—CH}_2\text{—}\underset{\underset{CH_2}{|}}{\overset{\overset{OH}{|}}{C}}\text{—R}^2 \\ \text{N}\overset{|}{\underset{\text{N}=\!=\!\!\!=\!\!\!=}{\diagdown}}\text{N} \end{array} \qquad (I)$$

| R | R¹ | R² | Z | p |
|---|---|---|---|---|
| 4-F-C₆H₄— | CH₃ | (CH₃)₃C— | — | 0 |
| 4-CH₃-C₆H₄— | CH₃ | (CH₃)₃C— | — | 0 |
| 2,4-Cl₂-C₆H₃— | CH₃ | (CH₃)₃C— | — | 0 |
| C₆H₅-CH₂— | CH₃ | (CH₃)₃C— | — | 0 |
| C₆H₅-CH₂-CH₂— | CH₃ | (CH₃)₃C— | — | 0 |
| C₆H₅— | CH₃ | (CH₃)₃C— | —C(=O)— | 1 |
| 4-CH₃-C₆H₄— | H | (CH₃)₃C— | —SO₂— | 1 |
| 4-CH₃-C₆H₄— | CH₃ | (CH₃)₃C— | —SO₂— | 1 |
| 4-Cl-C₆H₄— | CH₃ | (CH₃)₃C— | —SO₂— | 1 |
| (CH₃)₂CH— | H | 2-naphthyl | —C(=O)— | 1 |
| 4-CH₃-C₆H₄— | H | 2-naphthyl | —S(=O)₂— | 1 |

-continued $$\text{R}-(\text{Z})_p-\text{N}\underset{\underset{\text{R}^1}{|}}{\overset{\frown}{\underset{\smile}{}}}\text{N}-\text{CH}_2-\underset{\underset{\text{CH}_2-\text{N}(\text{N=CH-N=CH})}{|}}{\overset{\overset{\text{OH}}{|}}{\text{C}}}-\text{R}^2 \quad (I)$$

| R | R¹ | R² | Z | p |
|---|----|----|----|---|
| 2-chlorophenyl | CH₃ | 2-naphthyl | — | 0 |
| CH₂=CHCH₂— | H | 4-Cl-C₆H₄-CH₂-C(CH₃)₂— | —C(=O)— | 1 |
| 4-CH₃-C₆H₄— | H | 2,4-dichlorophenyl | —S(=O)₂— | 1 |
| 4-CH₃-C₆H₄— | H | 1-naphthyl | —S(=O)₂— | 1 |
| 2,4-dimethylphenyl | H | 4-Cl-C₆H₄-CH₂-C(CH₃)₂— | —C(=O)— | 1 |
| cyclopropyl | H | 2,4-dichlorophenyl | —C(=O)— | 1 |
| C₆H₅-CH=CH— | H | 2,6-dichlorophenyl | —C(=O)— | 1 |
| (CH₃)₃C—C≡C— | H | 2,4-dichlorophenyl | —C(=O)— | 1 |
| (CH₃)₂CH— | H | 5-chloro-2-[(CH₃)₂C(O—)]-pyridinyl | —C(=O)— | 1 |
| (CH₃)₂CH— | H | 3-CF₃-C₆H₄-O-C(CH₃)₂— | —C(=O)— | 1 |

-continued $$R-(Z)_p-N\underset{R^1}{\overset{}{\bigcirc}}N-CH_2-\underset{\underset{N\diagdown N}{\overset{OH}{|}}}{\overset{}{C}}-R^2 \quad (I)$$

| R | $R^1$ | $R^2$ | Z | p |
|---|---|---|---|---|
| $(CH_3)_2CH-$ | H | (5-chloro-2-methyl-thien-3-yl) | $-\underset{O}{\overset{}{C}}-$ | 1 |
| $(CH_3)_2CH-$ | H | (4-t-butylcyclohexyl) | $-\underset{O}{\overset{}{C}}-$ | 1 |
| phenyl | H | (2-naphthyl) | $-\underset{O}{\overset{}{C}}-$ | 1 |
| $CH_3OCH_2-$ | H | (2,4-dichlorophenyl) | $-\underset{O}{\overset{}{C}}-$ | 1 |
| $CF_3OCH_2-$ | H | (2,4-dichlorophenyl) | $-\underset{O}{\overset{}{C}}-$ | 1 |
| $(CH_3)_2CH-$ | H | $CF_3O-C_6H_4-O-C(CH_3)_2-$ | $-\underset{O}{\overset{}{C}}-$ | 1 |
| phenyl | H | (2,5-dimethylphenoxy)-C(CH_3)_2-CH_2-O- substituent | $-\underset{O}{\overset{}{C}}-$ | 1 |
| phenyl | H | $CH_2=CH-C(CH_3)_2-$ | $-\underset{O}{\overset{}{C}}-$ | 1 |

If, for example, 2-t-butyl-2-(1,2,4-triazol-1-yl)-methyl-oxirane and 1-phenyl-piperazine are used as starting materials, the course of the reaction of the process according to the invention can be represented by the following equation:

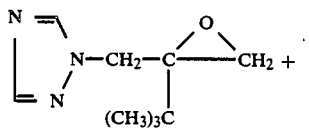

+

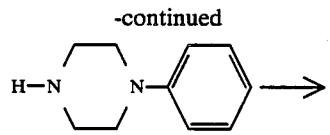

→

-continued

-continued

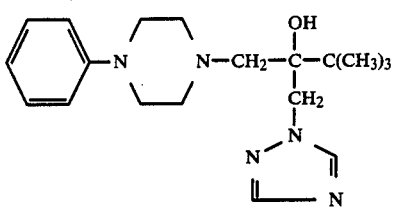

Formula (II) gives a general definition of the triazolylmethyloxiranes required as starting materials for carrying out the process according to the invention. Preferred compounds of the formula (II) are those in which $R^2$ represents those radicals which have already been mentioned in connection with the description of the substances according to the invention, of the formula (I), as being preferred for these substituents.

The triazolylmethyloxiranes of the formula (II) are known (see DE-OS (German Published Specification) No. 3,111,238) or can be prepared in an analogous manner by methods which are known in principle.

Formula (III) gives a general definition of the substituted piperazines furthermore required as starting materials for carrying out the process according to the invention. In this formula (III), R, $R^1$, Z and p preferably represent those substituents and indices which have already been mentioned in the description of the substances according to the invention, of the formula (I) as being preferred for these radicals and indices.

The piperazines of the formula (III) are generally known compounds of organic chemistry or can be prepared in a customary manner by generally known methods (see U.S. Pat. No. 4,258,188).

Suitable diluents for carrying out the process according to the invention are inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran or ethylene glycol dimethyl or diethyl ether, nitriles, such as acetonitrile or propionitrile, amides, such as dimethylformamide, dimethylacetamide and N-methylformamide, N-methylpyrrolidone or hexamethylphosphoric acid triamide, esters, such as ethyl acetate, sulphoxides, such as dimethylsulphoxide, and alcohols, such as methanol, ethanol, propanol or butanol.

The process according to the invention can, if required, be carried out in the presence of a catalyst. Particularly suitable catalysts are inorganic or organic bases.

These preferably include alkali metal carbonates, such as, for example, sodium carbonate and potassium carbonate, alkali metal hydroxides, such as, for example, sodium hydroxide; alkali metal alcoholates, such as, for example, sodium methylate, sodium ethylate, potassium methylate and potassium ethylate; alkali metal hydrides, such as, for example, sodium hydride; and lower tertiary alkylamines, cycloalkylamines and aralkylamines, such as, in particular, triethylamine.

In carrying out the process according to the invention, the reaction temperatures can be varied within a relatively wide range. In general, the reaction is carried out at temperatures between 20° C. and 180° C., preferably between 60° C. and 150° C.

The process according to the invention can be carried out under atmospheric pressure or under elevated pressure. When carried out under elevated pressure, a pressure of between 1 and 50 bar, preferably between 1 and 25 bar, is generally employed.

To carry out the process according to the invention, 1.0 to 5.0 moles, preferably 1.0 to 2.0 moles, of substituted piperazine of the formula (III) and, if appropriate, 0.1 to 2.0 moles, of a catalyst are generally employed per mol of the triazolylmethyloxirane of the formula (II). The reaction procedure, the working-up and the isolation of the reaction products of the formula (I) are carried out by generally customary methods.

All those acids which lead to physiologically acceptable salts are suitable for the preparation of acid addition salts of the compounds of the formula (I). Acids which are preferably used are those which have already been mentioned in connection with the description of the substances according to the invention as being acids preferred for the addition reaction.

The acid addition salts of the compounds of the formula (I) can be prepared in a simple manner by customary methods of salt formation. The procedure in general involves dissolving a compound of the formula (I) in a suitable inert diluent and then adding an acid. Isolation is effected in a known manner, for example, by filtering off the salt and, if required, purifying it by washing with an inert organic solvent.

Preferred salts for the preparation of metal salt complexes of the compounds of the formula (I) are salts of those metals which have already been mentioned in connection with the description of the substances according to the invention as being metals preferably used for the addition reactions. Anions of these metal salts are preferably derived from hydrohalic acids, such as, for example, hydrochloric acid and hydrobromic acid, as well as phosphoric acid, nitric acid and sulphuric acid.

The metal salt complexes of compounds of the formula (I) can be prepared in a simple manner by customary methods. In general, the procedure involves dissolving a metal salt in alcohol, such as, for example, ethanol, and then adding a compound of the formula (I). Isolation is likewise effected in a known manner, for example by filtering off the metal salt complex and, if required, purifying it by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The active compounds according to the invention can be used with particularly good success for combating cereal diseases, such as, for example, against the pathogens Pyrenophora eres, Cochliobolus sativus, Leptosphaeria nodorum or Fusarium species, for combating vegetable diseases, such as, for example, against the causitive organism Uromyces appendiculatus, for combating rice diseases, such as, for example, against the causative organism Pyricularia oryzae, and for combating mildew fungi and rust fungi. In addition, the active compounds according to the invention also have an excellent antimycotic and antiviral action and can be employed, for example, for combating Dermatophytes, yeasts and moulds in humans and animals.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic materials such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are in general between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.01% by weight, preferably 0.0001 to 0.02% by weight, are required at the place of action.

The preparation and use of the substances according to the invention are illustrated by the following examples.

PREKPARATION EXAMPLES

EXAMPLE 1

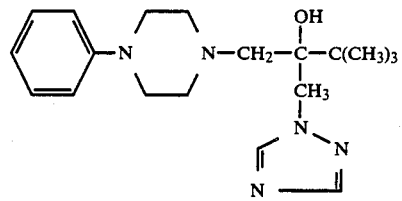

A mixture of 16.7 g (0.092 mol) of 2-t-butyl-1(1,2,4-triazol-1-yl)-methyl-oxirane and 16.2 g (0.1 mol) of 1-phenylpiperazine in 150 ml of ethanol is heated under reflux for 15 hours and then evaporated down under reduced pressure. The residue is taken up in ethyl acetate, and the solution is washed twice with water, dried over sodium sulphate and freed from the solvent under reduced pressure. After the crude product has been recrystallized from petroleum ether, 19 g (55% of theory) of 3,3-dimethyl-2-[(4-phenylpiperazin-1-yl)-methyl]-1-(1,2,4-triazol-1-yl)-butan-2-ol of melting point 99° C. to 100° C. are obtained.

The following piperazinylmethyl-1,2,4-triazolyl-methyl-carbinols of the formula (I) can be synthesized in a corresponding manner and in accordance with the general data for preparation:

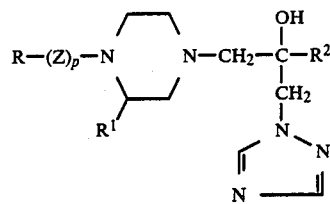
(I)
| Example No. | R | R¹ | R² | Z | p | Physical properties |
|---|---|---|---|---|---|---|
| 2 | 4-CH₃-C₆H₄- | H | $(CH_3)_3C-$ | — | 0 | M.p. 95–96° C. |
| 3 | 4-F-C₆H₄- | H | $(CH_3)_3C-$ | — | 0 | M.p. 109–110° C. |
| 4 | 3,4-Cl₂-C₆H₃- | H | $(CH_3)_3C-$ | — | 0 | M.p. 116° C. |
| 5 | 2-Cl-C₆H₄- | H | $(CH_3)_3C-$ | — | 0 | M.p. 86° C. |
| 6 | 2,3-(CH₃)₂-C₆H₃- | H | $(CH_3)_3C-$ | — | 0 | Oil |
| 7 | 4-(CH₃)₃C-C₆H₄- | H | $(CH_3)_3C-$ | — | 0 | M.p. 102–103° C. |
| 8 | 4-CH₃-C₆H₄- | CH₃ | $(CH_3)_3C-$ | — | 0 | M.p. 140–141° C. |
| 9 | 2,6-(CH₃)₂-C₆H₃- | H | $(CH_3)_3C-$ | — | 0 | M.p. 99–100° C. |
| 10 | C₆H₅-CH₂-CH₂- | H | $(CH_3)_3C-$ | — | 0 | M.p. 110–111° C. |
| 11 | 3-Cl-C₆H₄- | H | $(CH_3)_3C-$ | — | 0 | Oil |

-continued
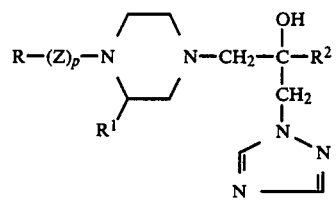
(I)
| Example No. | R | R¹ | R² | Z | p | Physical properties |
|---|---|---|---|---|---|---|
| 12 | benzyl (C₆H₅-CH₂-) | H | $(CH_3)_3C-$ | — | 0 | M.p. 101–102° C. |
| 13 | 3-(F₃C)-C₆H₄- | H | $(CH_3)_3C-$ | — | 0 | M.p. 78–79° C. |
| 14 | 4-Cl-2-CH₃-C₆H₃- | H | $(CH_3)_3C-$ | — | 0 | M.p. 101–102° C. |
| 15 | 4-Cl-2-CH₃-C₆H₃- (isomer) | H | $(CH_3)_3C-$ | — | 0 | M.p. 115–116° C. |
| 16 | 2-CH₃-C₆H₄- | H | $(CH_3)_3C-$ | — | 0 | M.p. 91–92° C. |
| 17 | 2,3-(CH₃)₂-C₆H₃- | H | $(CH_3)_3C-$ | — | 0 | M.p. 126–127° C. |
| 18 | 2-OCH₃-C₆H₄- | H | $(CH_3)_3C-$ | — | 0 | Oil |
| 19 | 4-Cl-3-(F₃C)-C₆H₃- | H | $(CH_3)_3C-$ | — | 0 | Oil |
| 20 | 3-CH₃-C₆H₄- | H | $(CH_3)_3C-$ | — | 0 | M.p. 84° C. |

-continued

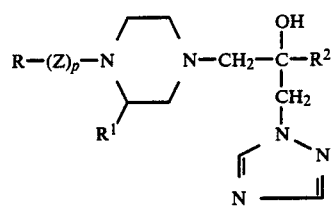
(I)

| Example No. | R | R¹ | R² | Z | p | Physical properties |
|---|---|---|---|---|---|---|
| 21 | 3,5-dichlorophenyl | H | $(CH_3)_3C-$ | — | 0 | M.p. 106–107° C. |
| 22 | 3-methoxyphenyl | H | $(CH_3)_3C-$ | — | 0 | Oil |
| 23 | $(CH_3)_2CH-$ | H | $(CH_3)_3C-$ | $-\underset{O}{\overset{\|}{C}}-$ | 1 | Oil |
| 24 | $(CH_3)_2CH-$ | H | 4-Cl-C₆H₄-CH₂-C(CH₃)₂- | $-\underset{O}{\overset{\|}{C}}-$ | 1 | M.p. 141° C. |
| 25 | $C_2H_5$ | H | 4-Cl-C₆H₄-CH₂-C(CH₃)₂- | $-\underset{O}{\overset{\|}{C}}-$ | 1 | M.p. 119° C. |
| 26 | $CH_3-(CH_2)_3-$ | H | 4-Cl-C₆H₄-CH₂-C(CH₃)₂- | $-\underset{O}{\overset{\|}{C}}-$ | 1 | 87–89° C. |
| 27 | $C_2H_5$ | H | 2-Cl-C₆H₄-CH₂-C(CH₃)₂- | $-\underset{O}{\overset{\|}{C}}-$ | 1 | Oil |
| 28 | $(CH_3)_2CH-$ | H | 2-Cl-C₆H₄-CH₂-C(CH₃)₂- | $-\underset{O}{\overset{\|}{C}}-$ | 1 | Oil |
| 29 | 2-chlorophenyl | H | 4-Cl-C₆H₄-CH₂-C(CH₃)₂- | — | 0 | |
| 30 | 3,4-dichlorophenyl | H | 4-Cl-C₆H₄-CH₂-C(CH₃)₂- | — | 0 | |

-continued

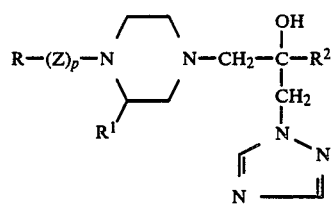

(I)

| Example No. | R | R¹ | R² | Z | p | Physical properties |
|---|---|---|---|---|---|---|
| 31 | (CH₃)₂CH—CH₂— | H | Cl—C₆H₄—CH₂—C(CH₃)₂—CH₃ | —C(=O)— | 1 | M.p. 94–96° C. |
| 32 | C₆H₅— | H | Cl—C₆H₄—CH₂—C(CH₃)₂—CH₃ | —C(=O)— | 1 | M.p. 140–141° C. |
| 33 | 4-biphenylyl | H | Cl—C₆H₄—CH₂—C(CH₃)₂—CH₃ | —C(=O)— | 1 | |
| 34 | 2-naphthyl | H | Cl—C₆H₄—CH₂—C(CH₃)₂—CH₃ | —C(=O)— | 1 | |
| 35 | (CH₃)₂CH— | H | Cl—C₆H₄—O—C(CH₃)₂—CH₃ | —C(=O)— | 1 | |
| 36 | (CH₃)₂CH— | H | Cl—C₆H₄—O—CH₂—C(CH₃)₂—CH₃ | —C(=O)— | 1 | |
| 37 | (CH₃)₂CH— | H | CH₃O—CH₂—C(CH₃)₂—CH₃ | —C(=O)— | 1 | |
| 38 | 4-biphenylyl | H | CH₃—CH₂—C(CH₃)₂—CH₃ | —C(=O)— | 1 | |
| 39 | 4-biphenylyl | H | Cl—C₆H₄—C(CH₃)₂—CH₃ | —C(=O)— | 1 | |
| 40 | 4-biphenylyl | H | Cl—C₆H₄—CH₂—CH(CH₃)— | —C(=O)— | 1 | |
| 41 | 4-CH₃—C₆H₄— | H | Cl—C₆H₄—CH₂—C(CH₃)₂—CH₃ | —C(=O)— | 1 | |

-continued
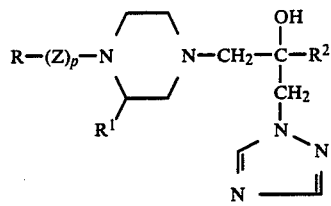
(I)
| Example No. | R | R¹ | R² | Z | p | Physical properties |
|---|---|---|---|---|---|---|
| 42 | 2,4-dichlorophenyl | H | 4-Cl-C6H4-CH2-C(CH3)2- | -C(=O)- | 1 | |
| 43 | 4-Cl-C6H4-O-CH2- | H | 4-Cl-C6H4-CH2-C(CH3)2- | -C(=O)- | 1 | |
| 44 | C6H5-CH2- | H | 4-Cl-C6H4-CH2-C(CH3)2- | -C(=O)- | 1 | |
| 45 | 4-(CH3)3C-C6H4- | H | 4-Cl-C6H4-CH2-C(CH3)2- | -C(=O)- | 1 | |
| 46 | 4-CH3O-C6H4- | H | 4-Cl-C6H4-CH2-C(CH3)2- | -C(=O)- | 1 | |
| 47 | C6H5- | H | 4-Cl-C6H4-CH2-C(CH3)2- | -SO2- | 1 | |
| 48 | 4-Cl-C6H4- | H | 4-Cl-C6H4-CH2-C(CH3)2- | -SO2- | 1 | |
| 49 | (CH3)2CH- | H | 2,4-dichlorophenyl | -C(=O)- | 1 | |
| 50 | 4-biphenyl | H | 2,4-dichlorophenyl | -C(=O)- | 1 | |
| 51 | C6H5- | H | 2,4-dichlorophenyl | -C(=O)- | 1 | |

-continued
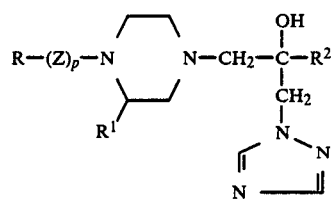
(I)
| Example No. | R | R¹ | R² | Z | p | Physical properties |
|---|---|---|---|---|---|---|
| 52 | 4-Cl-C₆H₄– | H | 2,4-Cl₂-C₆H₃– | –C(=O)– | 1 | |
| 53 | 4-Cl-C₆H₄– | H | 2,4-Cl₂-C₆H₃– | — | 0 | |
| 54 | cyclohexyl– | H | 4-Cl-C₆H₄–CH₂–C(CH₃)₂– | –C(=O)– | 1 | |
| 55 | CH₃– | H | 4-Cl-C₆H₄–CH₂–C(CH₃)₂– | –C(=O)– | 1 | M.p. 110–113° C. |
| 56 | 2,4-Cl₂-C₆H₃– | H | (CH₃)₃C– | –C(=O)– | 1 | Glass |
| 57 | 3,4-Cl₂-C₆H₃– | H | (CH₃)₃C– | –C(=O)– | 1 | M.p. 121° C. |
| 58 | 2,4-Cl₂-C₆H₃–O–CH₂– | H | (CH₃)₃C | –C(=O)– | 1 | Glass |
| 59 | 2-naphthyl | H | (CH₃)₃C | –C(=O)– | 1 | M.p. 117–9° C. |
| 60 | 4-(CH₃)₃C-C₆H₄– | H | (CH₃)₃C | –C(=O)– | 1 | M.p. 117–8° C. |
| 61 | (CH₃)₂CH– | H | 4-CH₃-C₆H₄–CH₂–C(CH₃)₂– | –C(=O)– | 1 | M.p. 117–8° C. |

-continued

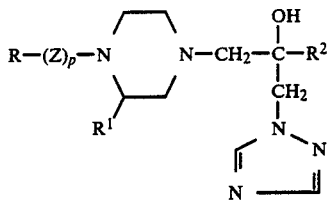

| Example No. | R | R¹ | R² | Z | p | Physical properties |
|---|---|---|---|---|---|---|
| 62 | (CH₃)₂CH—CH₂ | H | CH₃—⌬—CH₂—C(CH₃)₂— | —C(=O)— | 1 | Glass |
| 63 | C₆H₅— | H | CH₃—⌬—CH₂—C(CH₃)₂— | —C(=O)— | 1 | M.p. 154–5° C. |

USE EXAMPLES

In the use examples which follow, the compounds listed below were employed as comparative substances:

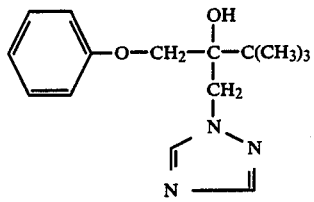

3,3-dimethyl-2-phenoxymethyl-1-(1,2,4-triazol-1-yl)-butan-2-ol

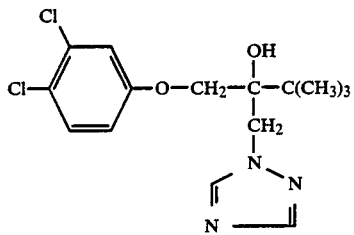

2-[(3,4-dichlorophenoxy)-methyl]-3,3-dimethyl-1-(1,2,4-triazol-1-yl)-butan-2-ol
(both disclosed in U.S. Ser. No. 549,867 filed Nov. 8, 1983).

Example A

Pyrenophora teres test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Pyrenophora teres. The plants then remain in an incubation cabinet at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, the substances according to the invention which are disclosed in Examples 5, 6, 7, 8, 9, 11, 13, 14, 15, 19, 20, 21, 24, 25, 26 and 31 show a substantially better activity than the comparative substance (A).

Example B

Uromyces test (dwarf beans)/protective

Solvent: 4.7 parts by weight of acetone
Emulsifier: 0.3 parts by weight alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous uredospore suspension of the bean rust causative organism (Uromyces appendiculatus) and remain in a dark humidity chamber at 20° to 22° C. and 100% relative atmospheric humidity for 1 day.

The plants are then placed in a greenhouse under intensive illumination at 20° to 22° C. and a relative atmospheric humidity of 70 to 80% for 9 days.

Evaluation is carried out 10 days after the inoculation.

In this test, the substances according to the invention which are disclosed in Examples 4, 11, 13, 14 and 15 show a substantially better activity than the comparative substance (B).

It will be understood that the specification and examples are illustrative but not limitative of the present invention and that other embodiments within the spirit and scope of the invention will suggest themselves to those skilled in the art.

What is claimed is:

1. A piperazinylmethyl-1,2,4-triazolyl-methyl-carbinol of the formula

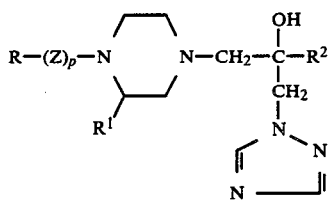

in which
- R is straight-chain or branched alkyl with 1 to 8 carbon atoms, straight-chain or branched alkenyl with 2 to 8 carbon atoms, cyclopropyl, cyclopentyl, cyclohexyl, or is phenyl, mono-, di- or tri- substituted phenyl the substituents being selected from the group consisting of fluorine, chlorine, methyl, ethyl, n-propyl, iso-propyl, tert.-butyl, methoxy, methylthio, trifluoromethyl, trifluoromethoxy and phenyl; or is naphthyl, phenethyl, benzyl or phenoxymethyl or phenoxymethyl which is substituted in the aromatic ring by 1 or 2 chlorine atoms;
- $R^1$ is hydrogen, methyl or ethyl;
- $R^2$ is methyl, ethyl, n-propyl, iso-propyl, n-butyl, tert.-butyl, cyclopropyl, cyclopentyl, cyclohexyl, phenyl, mono-, di- or tri-substituted phenyl the substituents being selected from the group consisting of fluorine, chlorine, methyl, trifluoromethyl and trifluoromethoxy; or
- $R^2$ is pyridyl, pyrimidyl or thienyl; or
- $R^2$ is a radical of the formula

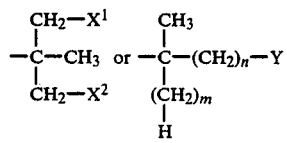

wherein
- $X^1$ is hydrogen or halogen,
- $X^2$ is halogen,
- Y is methyl, ethyl, n- or i-propyl, methoxy, ethoxy, methylthio, ethylthio, trifluoromethoxy, trifluoromethylthio, vinyl, allyl, methoxycarbonyl, ethoxycarbonyl or cyano, or represents phenyl, phenoxy, phenylthio, benzyloxy or benxzylthio, it being possible for each of the five last-mentioned radicals to be monosubstituted to tri-substituted in the phenyl part by fluorine, chlorine, bromine, methyl, ethyl, methoxy, methylthio, trifluoromethyl, trifluoromethoxy , trifluoromethylthio, dimethylamino, diethylamino, methoxycarbonyl, ethoxycarbonyl, cyano and/or nitro, or
- Y is pyridyloxy which is optionally substituted by chlorine,
- m is 0 or 1,
- n is 0, 1 or 2,
- Z is

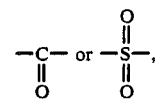

and
p is 0 or 1,
or an addition product thereof with an acid or metal salt.

2. A compound according to claim 1, wherein such compound is 2-[(4-(3,4-dichlorophenyl)-piperazin-1-yl)-methyl]-1-(1,2,4-triazol-1-yl)-butan-2-ol of the formula

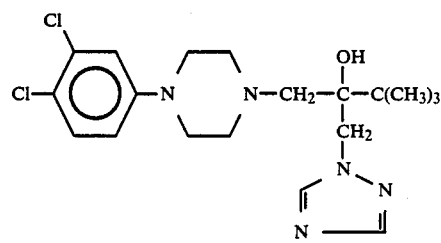

or an addition product thereof with an acid or metal salt.

3. A compound according to claim 1, wherein such compound is 2-[(4-(2-chlorophenyl)-piperazin-1-yl)-methyl]-1-(1,2,4-triazol-1-yl)-butan-2-ol of the formula

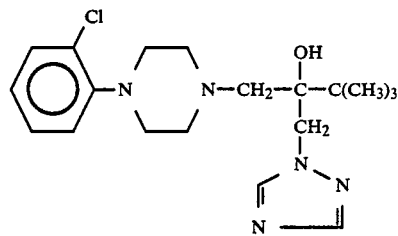

or an addition product thereof with an acid or metal salt.

4. A compound according to claim 1, wherein such compound is 2-[(4-(3-chlorophenyl)-piperazin-1-yl)-methyl]-1-(1,2,4-triazol-1-y)-butan-2-ol of the formula

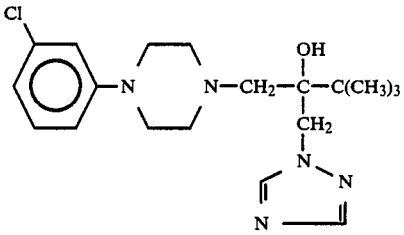

or an addition product thereof with an acid or metal salt.

5. A compound according to claim 1, wherein such compound is 1-(1,2,4-triazol-1-yl)-2-[(4-(3-trifluoromethylphenyl)-piperazin-1-yl-methyl]-butan-2-ol of the formula

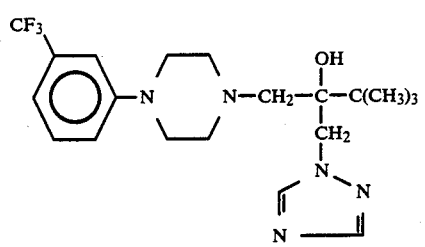

or an addition product thereof with an acid or metal salt.

6. A compound according to claim 1, wherein such compound is 1-[4-[(4-chloro-3-methyl-phenyl)-piperazine-1-yl)-methyl]-1-(1,2,4-triazol-1-yl)-butan-2-ol of the formula

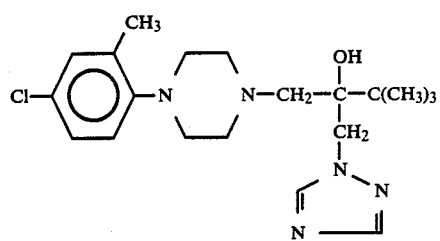

or an addition product thereof with an acid or metal salt.

7. A compound according to claim 1, wherein such compound is 2-[4-(4-chloro-3-trifluoromethyl-phenyl)-piperazin-1-yl)-methyl]-1-(1, 2,4-triazol-1-yl)-butan-2-ol of the formula

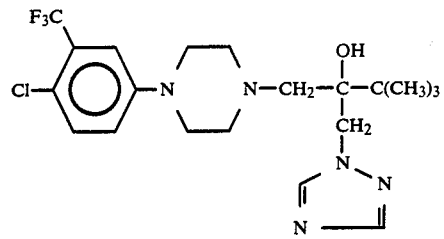

or an addition product thereof with an acid or metal salt.

8. A fungicidal composition comprising a fungicidally effective amount of a compound or addition product according to claim 1 in admixture with a diluent.

9. A method of combating fungi which comprises applying to such fungi or to a fungus habitat a fungicidally effective amount of a compound or addition product according to claim 1.

10. The method according to claim 9, wherein such compound is
2-[(4-(3,4-dichlorophenyl)-piperazin-1-yl)-methyl]-1-(1,2,4-triazol-1-yl)-butan-2-ol,
2-[(4-(2-chlorophenyl)-piperazin-1-yl)-methyl]-1-(1,2,4-triazol-1-yl)-butan-2-ol,
2-[(4-(3-chorophenyl)-piperazin-1-yl)-methyl]-1-(1,2,4-triazol-1-yl)-butan-2-ol,
1-(1,2,4-triazol-1-yl)-2-[(4-(3-trifluoromethylphenyl)-piperazin-1-yl-methyl]-butan-2-d,
1-[4-(4-chloro-3-methyl-phenyl)-piperazin-1-yl)-methyl]-1-(1,2,4-triazol-1-yl)-butan-2-ol or
2-[4-(4-chloro-3-trifluoromethyl-phenyl)-piperazin-1-yl)-methyl]-1-(1,2,4-triazol-1-yl) -butan-2-ol
or an addition product thereof with an acid or metal salt.

* * * * *

UNITED STATES PATENT AND TRADEMARK OFFICE
CERTIFICATE OF CORRECTION

PATENT NO. : 4,738,962
DATED : April 19, 1988
INVENTOR(S) : Graham Holmwood, et al.

It is certified that error appears in the above-identified patent and that said Letters Patent is hereby corrected as shown below:

| | |
|---|---|
| Col. 14, line 64 | Delete "eres" and substitute --teres-- |
| Col. 14, line 67 | Correct spelling of --causative-- |
| Col. 16, line 40 | Correct spelling of --PREPARATION-- |
| Col. 32, line 49 | After "-1-" second instance delete "y" and substitute --yl-- |
| Col. 33, line 16-17 | Correct --piperazin-- |
| Col. 34, line 30 | After "2-" delete "d" and substitute --ol-- |

Signed and Sealed this

Eighteenth Day of October, 1988

Attest:

DONALD J. QUIGG

Attesting Officer

Commissioner of Patents and Trademarks